(12) United States Patent
Merboth et al.

(10) Patent No.: US 7,018,382 B2
(45) Date of Patent: Mar. 28, 2006

(54) BONE MARROW MIXING INSTRUMENT

(75) Inventors: Barbara L. Merboth, Bridgewater, NJ (US); Arthur A. Genzman, Stony Point, NY (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 265 days.

(21) Appl. No.: 10/704,813

(22) Filed: Nov. 12, 2003

(65) Prior Publication Data

US 2005/0101963 A1    May 12, 2005

(51) Int. Cl.
     *A61B 17/56*      (2006.01)
(52) U.S. Cl. .......................................... 606/93
(58) Field of Classification Search ............... 606/92, 606/93, 94; 604/82–84; 222/136–138, 391
See application file for complete search history.

(56) References Cited

U.S. PATENT DOCUMENTS

| | | | | |
|---|---|---|---|---|
| 4,452,285 A | * | 6/1984 | Leibhard et al. | ............. 141/392 |
| 4,471,888 A | * | 9/1984 | Herb et al. | ................... 222/137 |
| 4,566,610 A | * | 1/1986 | Herb | ........................... 222/137 |
| 4,826,053 A | | 5/1989 | Keller | |
| 5,364,386 A | * | 11/1994 | Fukuoka et al. | ............. 604/411 |
| 5,520,658 A | * | 5/1996 | Holm | ........................... 604/191 |
| 5,638,997 A | * | 6/1997 | Hawkins et al. | ............. 222/391 |
| 5,824,084 A | | 10/1998 | Muschler | |
| 6,030,214 A | * | 2/2000 | Zwingenberger | .............. 433/82 |
| 6,047,861 A | * | 4/2000 | Vidal et al. | ................... 222/137 |
| 6,049,026 A | | 4/2000 | Muschler | |
| 6,382,466 B1 | * | 5/2002 | Schneider et al. | ........... 222/137 |
| 6,394,982 B1 | * | 5/2002 | Ehrenfels | ..................... 604/191 |
| 6,425,897 B1 | * | 7/2002 | Overes et al. | ................. 606/93 |
| 6,585,696 B1 | * | 7/2003 | Petersen et al. | ............. 604/191 |
| 6,889,872 B1 | * | 5/2005 | Herman et al. | ................ 222/82 |

OTHER PUBLICATIONS

J. Goshima et al., "The Origin of Bone Formed in Composite Grafts of Porous Calcium Phosphate Ceramic Loaded with Marrow Cells", *Clinical Orthopaedics and Related Research*, vol. 269 (1991).

* cited by examiner

*Primary Examiner*—Eduardo C. Robert
*Assistant Examiner*—Richard Shaffer
(74) *Attorney, Agent, or Firm*—John S. Hale; Gipple & Hale

(57) ABSTRACT

The bone marrow mixing instrument having a handle housing with a trigger mounted thereto. The handle housing contains a ratchet drive feed mechanism with a pawl assembly and a moveable ratchet bar. The other end of the ratchet bar is secured to a mixing housing which holds syringes filled with material and defines channels leading from the syringe area to a mixing nozzle removably mounted to the mixing housing. A piston rod and piston are mounted in each syringe containing bone defect material with a piston being advanced within the respective syringe by the feed mechanism to discharge bone defect material from the syringe into the adjacent channels in the mixing housing and into the mixing nozzle.

38 Claims, 8 Drawing Sheets

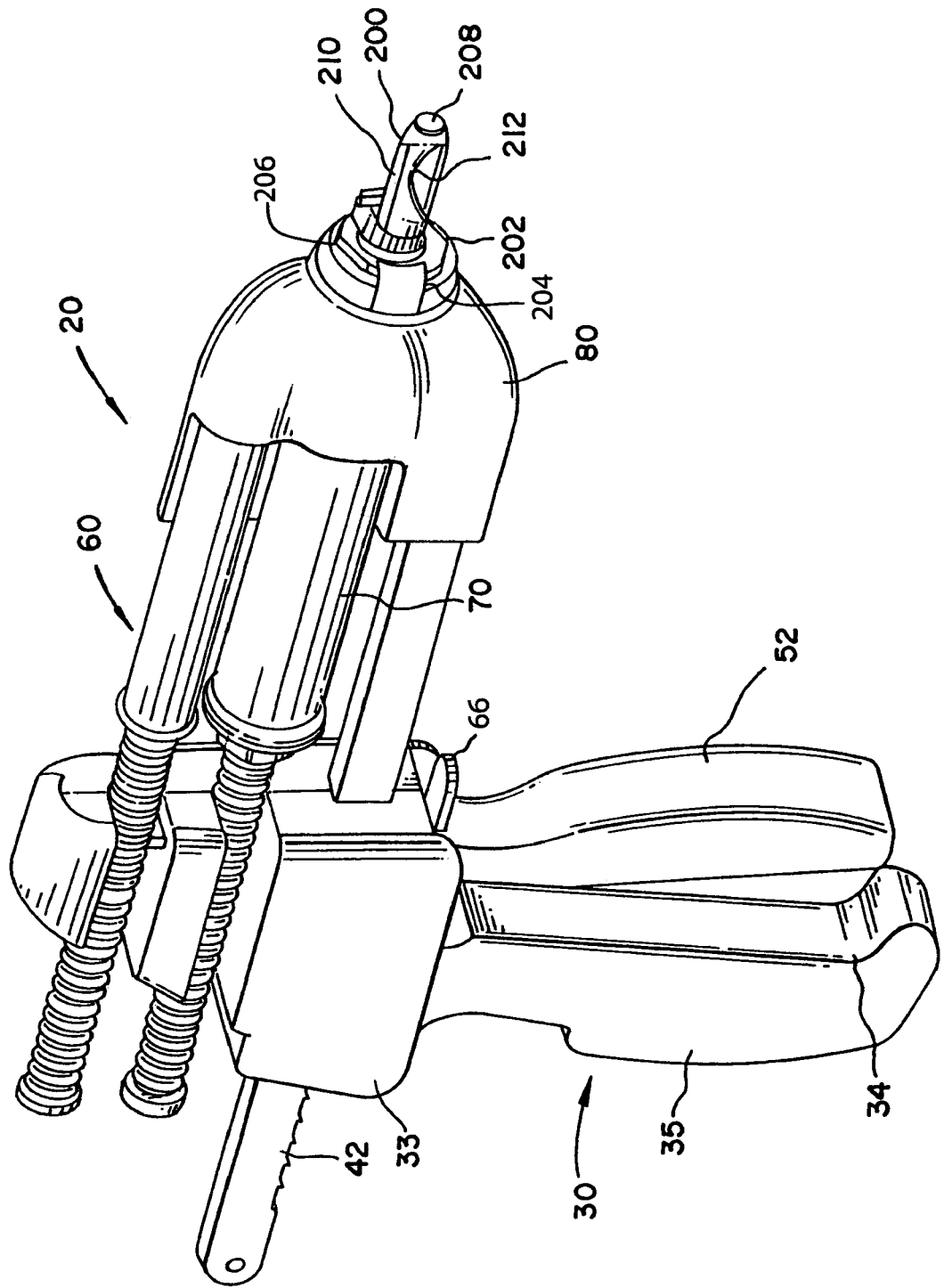

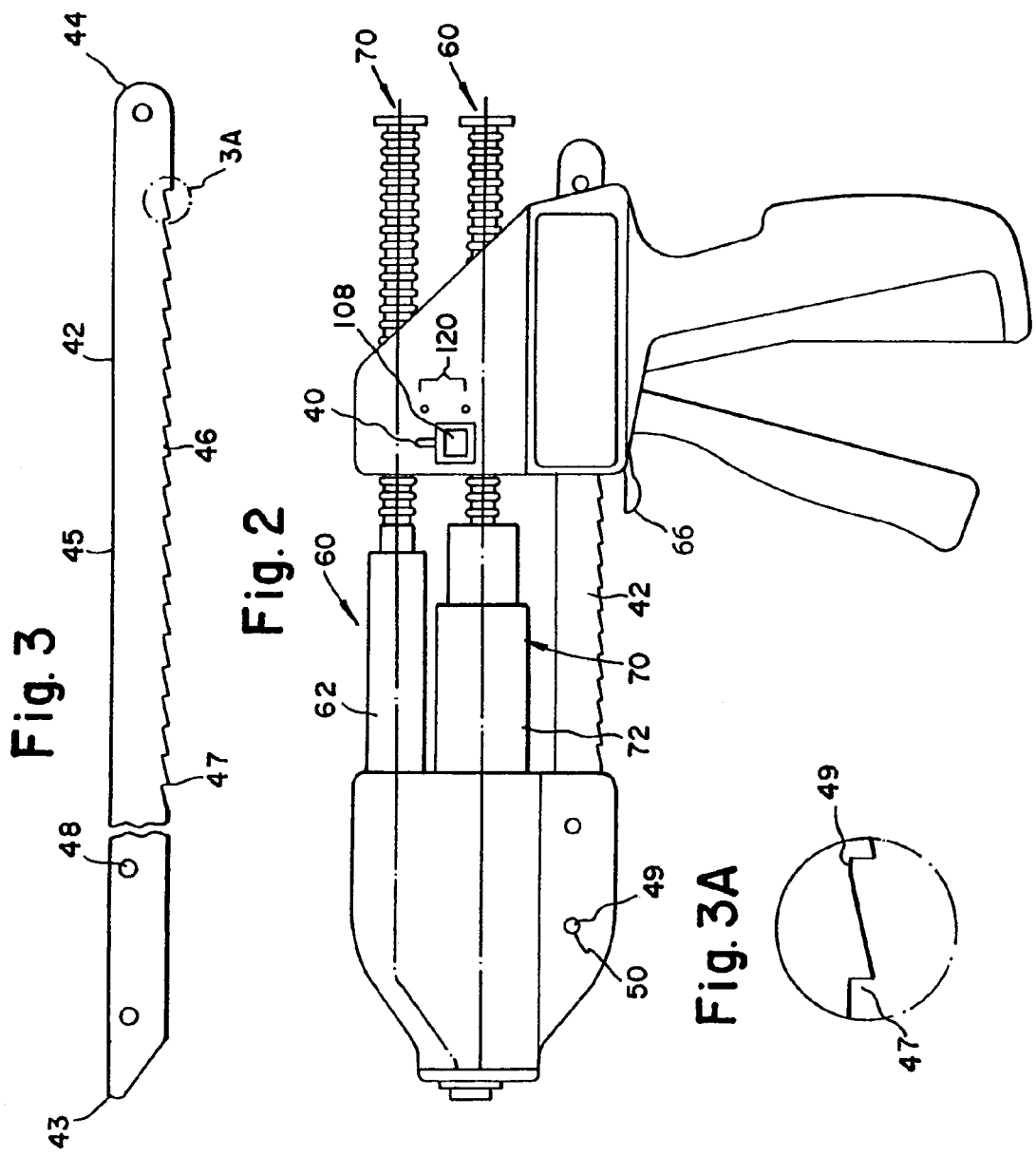

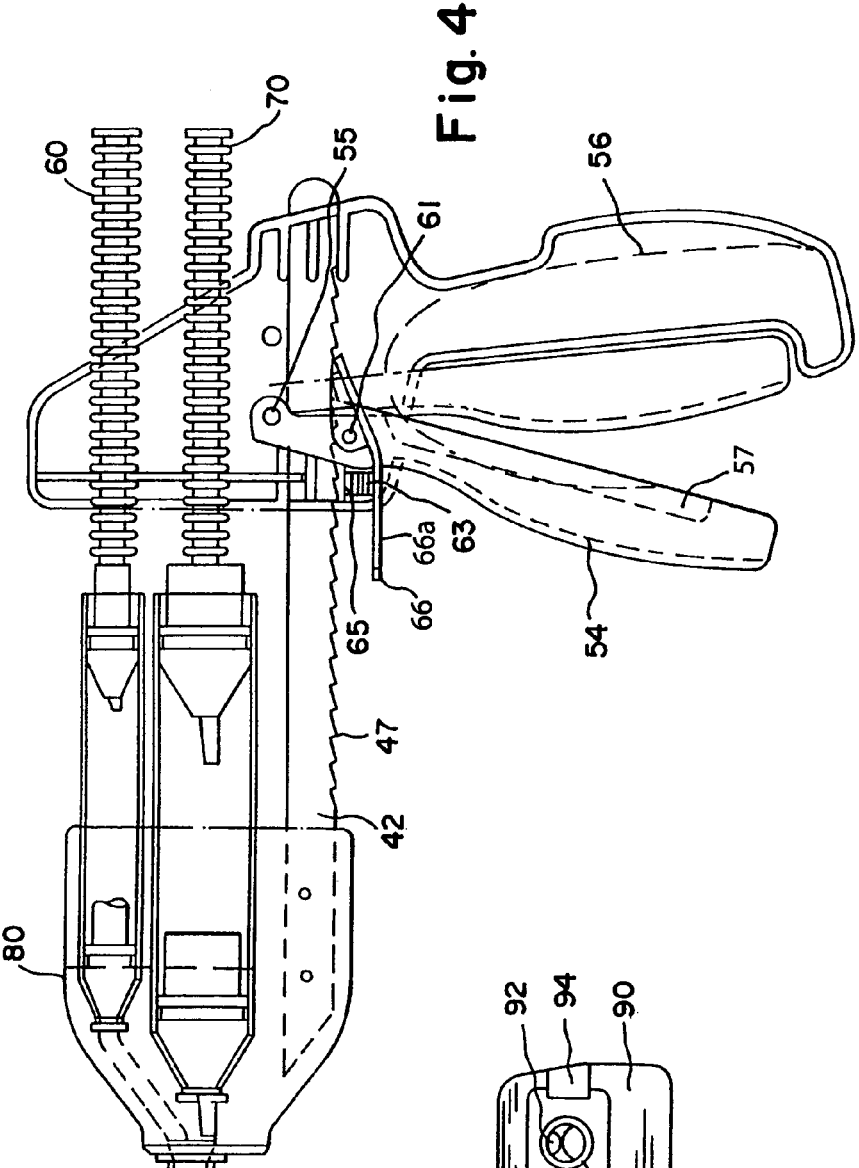

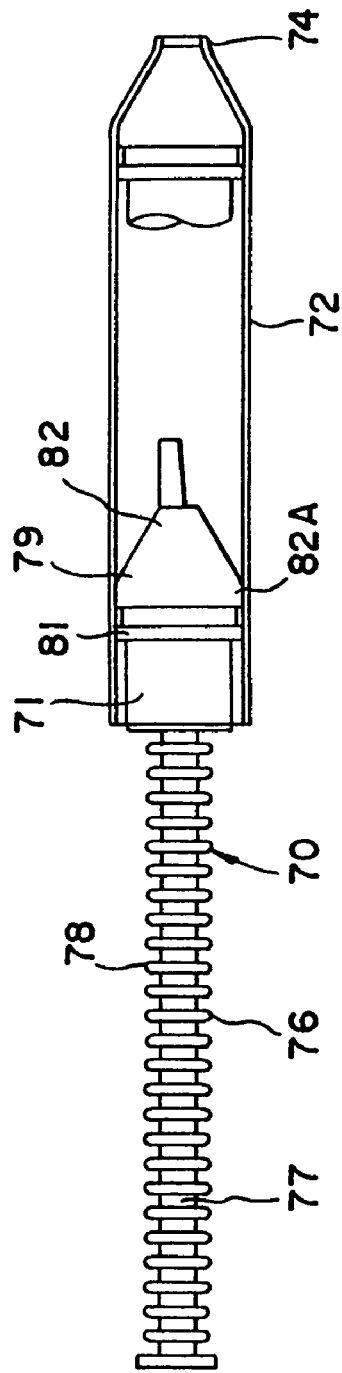
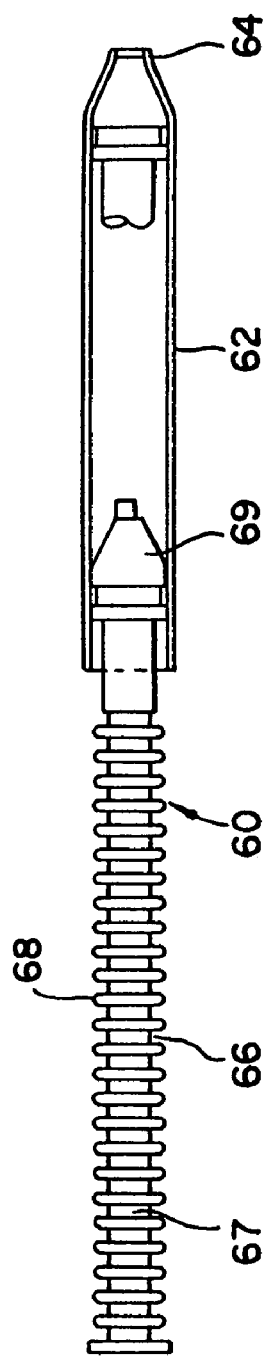

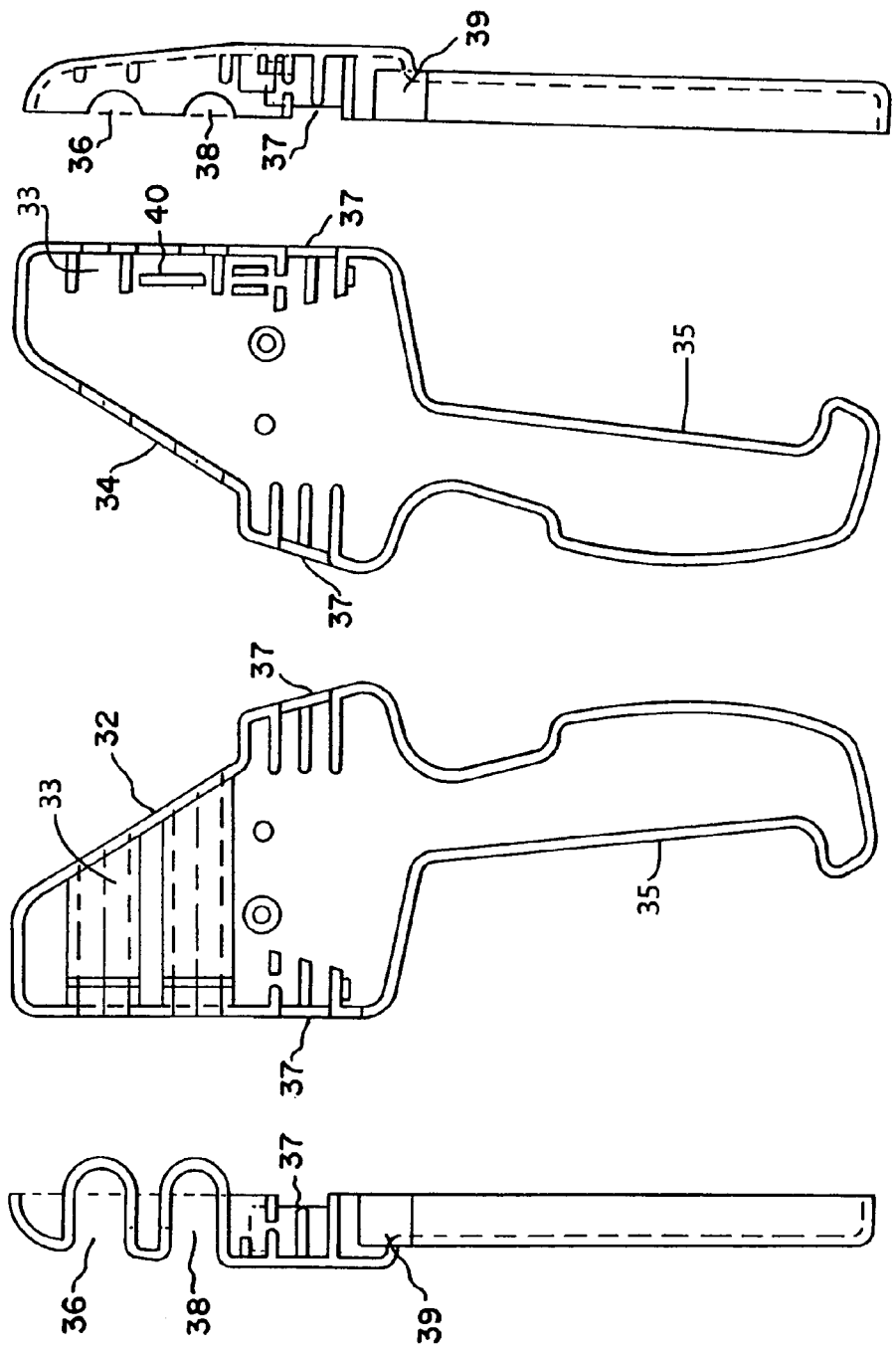

BONE MARROW MIXING INSTRUMENT

RELATED APPLICATIONS

There are no related applications.

FIELD OF THE INVENTION

The present invention generally relates to a bone marrow mixing instrument for the repair and replacement of the various portions of the human skeletal system. The present invention is specifically directed to provide a bone marrow mixing instrument having two cartridges, one containing bone marrow and one containing a scaffolding material such as demineralized bone material mounted on a pistol type handle with a trigger activated feeding mechanism. The bone marrow and scaffolding material composition is driven by a dual plunger/piston assembly into a mixing housing and exits the mixing housing via a nozzle on to the bone defect site.

BACKGROUND OF THE INVENTION

Bone grafting is widely used to treat fractures and bone defect areas. Autogenous cancerous bone, which is taken from one site in the graftee and implanted in another site in the graftee, is currently the most effective bone graft and provides the scaffolding to support the distribution of the bone healing response and also provides the connective tissue progenitor cells which form new cartilage or bone. However, the harvest of autogenous bone results in significant cost and morbidity, including scars, blood loss, pain, prolonged operative and rehabilitation time and risk of infection. Furthermore, in some clinical settings, the volume of material necessary at the graft site can exceed the volume which can be extracted from the available autograft. Accordingly, alternatives to autografts have been developed in an attempt to reduce the problem of morbidity and cost of bone grafting procedures.

Several purified or synthetic materials, including ceramics, biopolymers, processed allograft bone and collagen-based matrices have been investigated or developed to serve as substitutes for autografts. The FDA has approved a porous coral derived synthetic hydroxyapatite ceramic for use in contained bone defects. A purified collagen/ceramic composite material is also approved for use in acute long bone fractures. Although these materials avoid the morbidity involved in harvesting autografts from the graftee and eliminate problems associated with a limited amount of available autograft, the clinical effectiveness of the synthetic materials generally is less than autografts.

Synthetic graft materials have also been used as carriers for bone marrow cells. When such composite materials have been implanted into skeletal defects, the connective tissue progenitor cells differentiated into skeletal tissue. In some instances, composite implants were made by soaking the synthetic graft material in a cell suspension obtained from bone marrow. However, the connective tissue progenitor cells, which have the capacity to differentiate into cartilage, bone and other connective tissue such as fat, muscle, and fibrous tissue are present in the bone marrow in very minute amounts. The numbers of such cells present in 1 ml of bone marrow varies widely from subject to subject ranging from about 100 cells to 20,000 cells depending to large extent on the age of the donor. This represents a mean of about one in 20,000 to one in 40,000 of the nucleated cells in bone marrow.

Demineralized bone material from allogenic sources has been available for over fifty years and has been demonstrated to facilitate healing of bony defects created by trauma, disease or surgical intervention. Demineralized bone material (DBM) is provided as a dry powder and in various carriers to improve the convenience of handling and wound placement. DBM acts as an osteoconductive scaffold as well as having some osteoinductive properties (ability to induce surrounding patient cells to grow new bone) by virtue of bone morphogenetic proteins (BMP's) retained in the DBM after the demineralization process.

Surgeons have previously used autologous bone, bone marrow and patient blood to provide osteoprogenitor cells to facilitate healing of bony defects. These procedures are highly effective to propagate new bone growth and accelerate wound healing. The use of bone chips and bone marrow taken from the patient's hip (iliac crest) or vertebral intertransverse processes, while providing an effective supply of osteogenic material, creates significant patient morbidity.

As an alternative, bone marrow can be aspirated from the patient, usually from the iliac crest, vertebral body sternum or long bone condyle. This bone marrow aspirate (BMA) contains blood serum, red blood cells and some specific osteoprogenitor cells known as mesenchymal stem cells (MSC) or pluripotential cells. Orthopaedic surgeons have used bone marrow aspirate to facilitate wound healing in spinal fusion, fracture management or other skeletal defects. BMA alone is a slightly viscous, sticky liquid and is difficult to manage for delivery to an operative surgical location. Some workers have mixed BMA with demineralized bone matrix and gotten superior healing rates.

The traditional and current technique involves removing BMA through a bone perforation biopsy-type device and collecting the BMA in a sterile syringe. The BMA is then discharged from the syringe into a container in the operating room. The DBM is then added to the BMA and manually mixed. DBM is provided in a sterile, freeze-dried granular form and delivered from a container, usually a glass bottle.

This manual procedure makes it difficult to control the mix ratio. It may also compromise sterility, as the mixing is being done in the open in the operating room. Once mixed, the formulation may be held for a time ranging from a few minutes to up to an hour and risk drying out and becoming even more difficult to manipulate in the defect area. Finally, the delivery from the mixing container is usually done with a spatula, which results in waste, namely, material being left behind in the container and a loss of the precious bone and marrow cells. Vigorous mixing may also damage the cells in the marrow. The present invention thus overcomes these procedures which are difficult to implement: namely; time constraints, loss of sterility, preservation of cell viability and eliminate waste of material.

The prior art has attempted to solve the problems which occur in mixing bone marrow with a scaffolding material. Isolated marrow cells from quail, in solution, were implanted or delivered via soaking in blocks of calcium phosphate ceramics, the soaked blocks being deposited in subcutaneous sites in a nude mouse. The osteogenesis is a biphasic phenomena in which donor cells are largely responsible for osteogenesis in the first three to four weeks and in the second phase, eight to twelve weeks post surgery the host cells actions predominate and begin to show the formation of marrow of host origin. "The Origin of Bone Formed in Composite Grafts of Porous Calcium Phosphate Ceramic Loaded with Marrow Cells", by J. Goshima et al., Clinical Orthopaedics and Related Research, vol. 269, pp. 275–283 (1991) Also of interest in this reference is the discussion of prior art on page 281, col. 1.

The use of a bone marrow cells in a bone graft is shown in several U.S. patents, namely, U.S. Pat. No. 5,824,084, issued Oct. 20, 1998 and U.S. Pat. No. 6,049,026 issued Apr. 11, 2000. These patents are directed toward a method for preparing a composite bone graft which includes providing a bone marrow aspirate suspension and passing the bone marrow aspirate suspension through a porous, biocompatible, implantable substrate, such as coralline hydroxyapatite, mineralized or demineralized cancerous bone sections, granules of demineralized bone, sintered cortical or cancerous bone and granular ceramics, to provide a composite bone graft having an enriched population of connective tissue progenitor cells. Because the method is preferably performed intraoperatively it reduces the number of occasions the graftee must undergo invasive procedures. The composite graft includes an enriched population of connective tissue progenitor cells and a greater number of connective tissue progenitor cells per unit volume than that found in the original bone marrow aspirate.

It is also known in the art to use a piston ram carried in a trigger activated gun type device to dispense material carried a cartridge which is loaded into the gun type device. A representative patent showing this type of dispenser is shown in U.S. Pat. No. 4,826,053 issued May 2, 1989.

SUMMARY OF THE INVENTION

The present invention is directed toward a pistol type bone marrow and demineralized bone mixing instrument utilizing a trigger which activates a rachet drive to advance plunger pistons in stacked syringe tubes containing demineralized bone material and bone marrow thus driving the same into a mixing head which discharge the mixed components at a predetermined ratio.

It is an object of the invention to provide a bone marrow mixing instrument having an ergonomically shaped pistol type handle to assist a physician in inserting mixed bone and bone marrow into a patient's defect site.

It is still another object of the invention to provide a bone marrow mixing instrument having a magazine which holds loaded syringe cartridges.

It is yet another object of the invention, to provide for the mixing of DBM or other scaffolding material with bone marrow of the patient being operated upon at a predetermined ratio conducive to bone healing.

It is a further object to provide a bone marrow instrument which mixes the bone marrow with a scaffolding material while precluding cell damage to the bone marrow cells.

It is still another object of the invention to provide a bone marrow mixing instrument having a locking member which holds the piston rods and piston heads in a fixed locked position inside syringe tubes used in the instrument.

It is yet another object of the invention to provide a bone marrow mixing instrument which allows different nozzles having different mixing characteristics to be selectively mounted to the bone mixing instrument.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

BRIEF DESCRIPTION OF THE DRAWINGS

FIG. 1 is a perspective view of the inventive bone marrow mixing instrument;

FIG. 2 is a side elevational view of the bone marrow mixing instrument of FIG. 1 showing the plungers axes;

FIG. 3 is an enlarged partial side view of the rachet bar of the mixing instrument;

FIG. 3A is an inverted enlarged tooth detail of the rachet bar of FIG. 3 taken from circle 3A;

FIG. 4 is a side elevational view of the bone marrow mixing instrument of FIG. 1 with various components shown in either cross section or phantom;

FIG. 5 is a top plan view of the bone marrow mixing instrument of FIG. 4 showing the line of travel of the piston of the piston heads and piston rods;

FIG. 5A is an enlarged isolated front view of the connector member shown in FIGS. 4 and 5;

FIG. 6 is an enlarged isolated partial sectional view showing sequential movement of the piston head in the syringe barrel of the bone material plunger assembly;

FIG. 7 is an enlarged isolated partial sectional view showing sequential movement of the piston head in the syringe barrel of the bone marrow mixing plunger assembly;

FIG. 14 is a front view of the left section of the handle housing;

FIG. 15 is a side inner view of the section of the handle housing shown in FIG. 14;

FIG. 16 is a side inner view of the section of the handle housing shown in FIG. 17;

FIG. 17 is a front view of the right section of the handle housing;

DETAILED DESCRIPTION OF THE INVENTION

Figure 8:
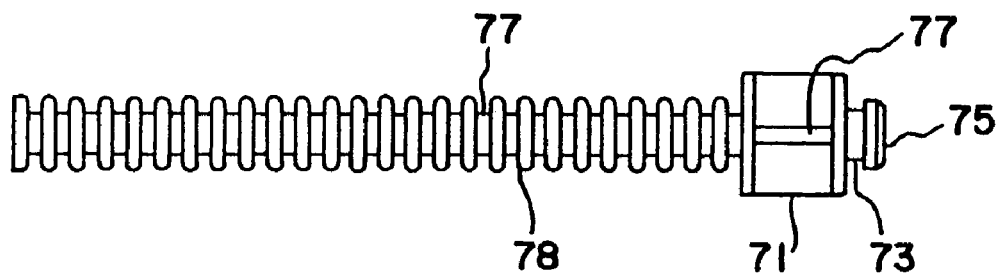
FIG. 8 is a side elevational view of the piston rod shown in FIG. 6.

The preferred embodiment and best mode of the invention is shown in FIGS. 1 through 22. While the invention is described in connection with certain preferred embodiments, it is not intended that the present invention be so limited. On the contrary, it is intended to cover all alternatives, modifications, and equivalent arrangements as may be included within the spirit and scope of the invention as defined by the appended claims.

The present invention is directed to a gun type bone marrow mixing instrument 20 for receiving bone marrow collected from a patient, mixing it with mineralized bone material, demineralized or partially demineralized bone material (DBM) such as DBX® manufactured by the Musculoskeletal Transplant Foundation, ceramics or other biocompatible materials in a predetermined precise ratio of marrow to DBM and delivering it directly to a bone defect site via a closed system. The DBM is in a pre-mixed form in a viscous excipient such as sodium hyaluronate or its derivation (HA). The HA is best formulated at physiological pH (6.5–7.5) and isotonic osmolality (250~330 in Osmol/kg).

The delivery of bone marrow aspirate (BMA) into the surgical defect is difficult. The ratio of BMA to DBM is important. If there is too little BMA, the mixture is dry, grainy and has only a limited number of the osteogenic MSC's. Too much BMA and the mixture may be excessively sticky and of low viscosity, making it difficult to place the mixture in the operative site and problematical to retain it in position. Optimal ratios of BMA to DBM range from 1:1 to 6:1 (v/v) with a preferred ratio being 1:3.

The bone marrow mixing instrument 20 is constructed with a premolded handle assembly 30 having a rachet drive assembly 40 mounted therein which is advanced by a trigger mechanism 52 so that dual plunger or piston assemblies 60 and 70 as more clearly shown in FIGS. 6 and 7 are driven into their respective syringe tubes or barrels 62 and 72 to discharge the respective materials contained therein (bone marrow aspirate and scaffolding material) outside of the distal ends 64 and 74 of the respective syringe tubes. The demineralized bone material is preferably preloaded in a sterilized syringe tube in a kit together with a sterilized syringe for the BMA together with the respective plunger or piston assemblies for the syringe tubes which are described in detail below. The drive housing assembly 33 is formed with two sections 32 and 34 which are molded halves and are preferably heat sealed together or sealed with a suitable adhesive. Each half contains a drive housing section 33 and a handle section 35. The handle section 35 has a hollow interior with piston rod seats 36 and 38 and defines rachet bar slots 37 and pawl slots 39. The right handle section 34 is provided with a locking slot 40 through which locking member shaft 106 protrudes. The outer surface of the handle section is marked with colored lock and unlock indicia 120 adjacent the shaft knob 108 as seen in FIG. 2 which may be in the form of dots or lines to indicate locked and unlocked positions. The handle is preferably constructed of a suitable plastic which can be autoclaved or easily sterilized.

A toothed rachet bar 42 is mounted in handle slots 37. The rachet bar 42 is constructed of stainless steel 316 having an angled distal end 43 and a rounded proximal end 44 as shown in FIG. 3. One end wall 45 of the bar 42 is planar and the other end wall 46 has a plurality of teeth 47 disposed therein. The teeth are shown in more detail in FIG. 3A and have a pitch of 0.204±0.002 inches with a flat tooth surface 49 of 0.030 inches. The distal end 43 has several through-going apertures 48 which are adapted to receive pins 49 which are inserted through holes 50 formed in the mixing housing 80.

Figure 9:
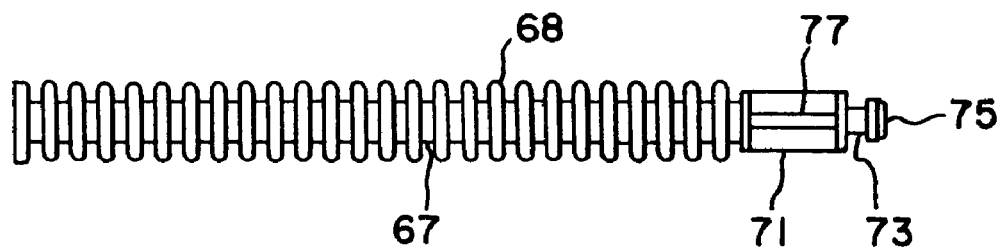
FIG. 9 is a side elevational view of the piston rod shown in FIG. 7.
Figure 10:
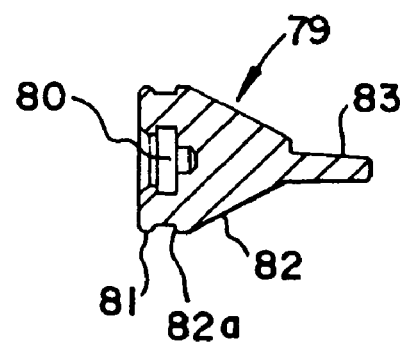
FIG. 10 is an enlarged cross sectional view of a piston head shown in FIG. 6.

The piston or plunger assemblies 60 and 70 have their respective piston rods 66,76 mounted in seats 36 and 38 formed in the handle. The piston rods 66, 76 of the piston assemblies each are formed with a central rod 67, 77 around which a plurality of spaced circular retainer members 68, 78 are placed. The spaced circular retainer members 68,78 which are preferably 0.062±0.002 inches in width extend outward from the respective central rod and are spaced the same distance from each other to receive a locking member 100 as described below. As shown in FIGS. 8 and 9 each central piston rod terminates in a piston head retainer member 71 which has transverse fins 77 with circular caps on each end or the retainer member is alternatively square. A post 73 extends from the distal cap and terminates in a head member 75 of a greater diameter then the post 73 with a rounded outer surface. The post 73 and head 75 snap fits into a stepped blind bore 80 of a resilient piston head 69/79. The piston head 69, 79 as shown in FIGS. 6, 7 and 10 defines a cylindrical stepped end chamber 80 which fits over piston head member 75, a circular end ring 81 and a cone shaped head 82 which fits into the tapered syringe tube distal end (64,74). The cone shaped head can be provided with various tips 83 as shown in FIGS. 4 and 10. The larger diameter of the cone shaped head 82a has a diameter equal to or slightly larger than that of the circular ring 81 and tightly fits into the barrel of the respective syringe and is slidably moved therein The piston head is preferably made of Helvot Pharma FM 257/2 or equivalent manufactured by Precision Polymer Products Inc. and is silicone coated with Nu-Sil MED—360cs or equivalent.

The trigger mechanism 52 comprises a trigger body 54 which is mounted by a pin 55 to the handle assembly 30. The pin 55 extends through bores 55a The trigger body 54 defines a spring cavity 57 which holds one end of a bracing spring 56, the other end being held in a handle so that the trigger body 54 is continuously biased away from the handle. The biasing spring 56 as shown in phantom in FIG. 4 is preferably 0.010 spring stainless steel. The other end of the trigger body defines a yoke 58 with a closed distal end 59. The trigger mechanism is mounted to the handle housing by a pin 55. A pawl 66 is mounted on a pin 61 which is mounted in bore 61a cut into the yoke arms and extends across the yoke arms. The pin is preferably made of stainless steel 316 and is structured so that it is chamfered at one end and has a head on the opposite end. One end 66a of the pawl 66 is biased downward by a coil spring 63 which engages the planar upper surface of the pawl with the other end of the coil spring being mounted around a post 65 integrally formed with the handle housing. Since the pawl 66 is bent as can be seen in FIG. 4, the other end adjacent the pin seat engages the toothed surface 46 of the rachet bar driving the rachet bar one tooth length rearward as the trigger is pulled. When the pawl 66 is driven backward and upward by action of the trigger body, the rear end of the pawl engages a tooth 47 of the rachet bar to drive the same one tooth length of the rachet bar.

Figure 11:
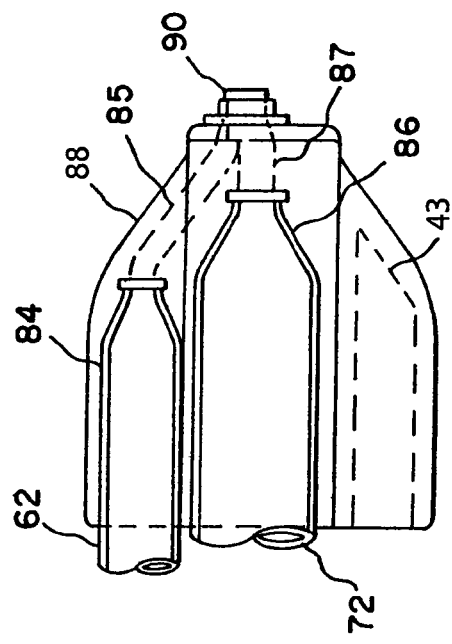
FIG. 11 is an enlarged partial side view in phantom of the mixing housing of the instrument of FIG. 1.
Figure 12:
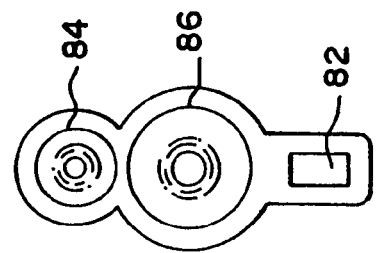
FIG. 12 is a front elevation view of the mixing magazine of FIG. 11.
Figure 13:
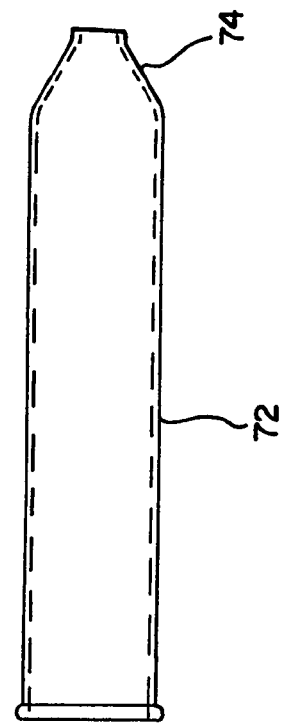
FIG. 13 is a side elevational view of a syringe barrel used in the invention with side walls shown in phantom.
Figure 18:
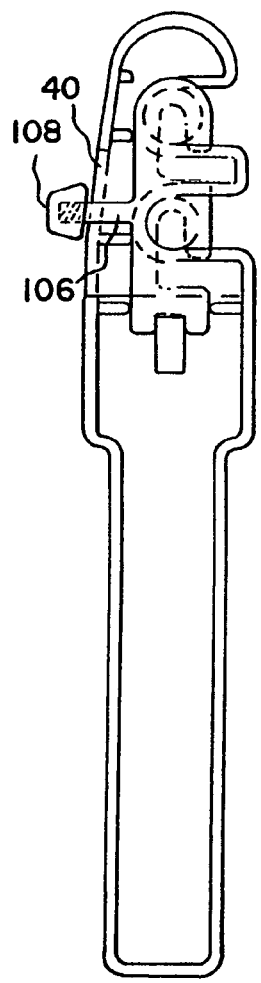
FIG. 18 is a rear cross sectional view of the handle assembly showing the locking mechanism.

The small syringe tube 62 preferably contains bone marrow previously collected by the surgeon from the patient while the larger syringe tube 72 contains a demineralized or partially demineralized bone material which has been previously placed in the syringe in a sealed sterile condition. Both syringe tubes 62 and 72 are mounted in chambers 84 and 86 respectively which are formed in the mixing housing as shown in FIG. 11. Different syringe tube diameters can be provided to obtain the ratio of mixture desired. The syringe tube holding portion of the mixing housing has a figure 8 cross section.

Figure 19:
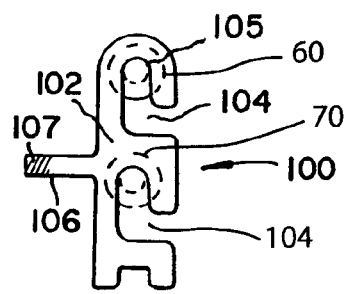
FIG. 19 is an isolated plan view of the locking plate shown in FIG. 18 with the piston rod shown in phantom.
Figures 20, 21:
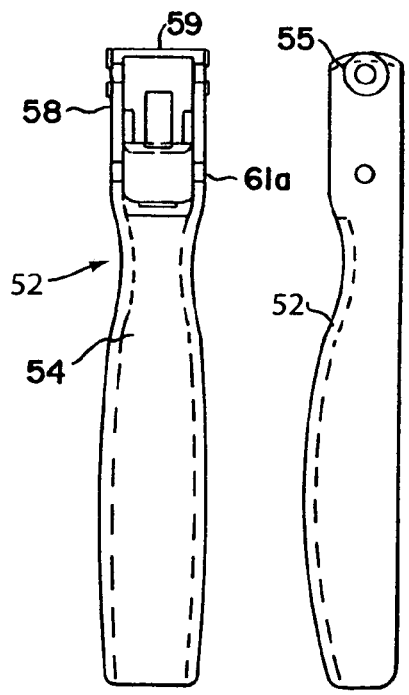
FIG. 20 is a front elevational view of the trigger member.
FIG. 21 is a side view of the trigger member shown in FIG. 20.
Figure 22:
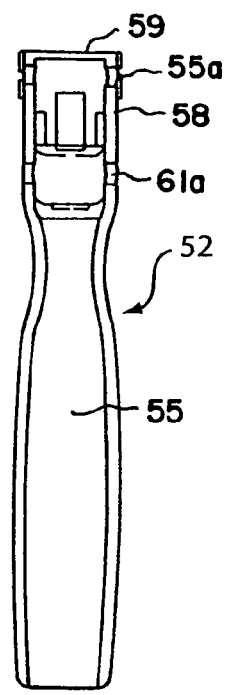
FIG. 22 is a rear view of the trigger member shown in FIG. 20.

A locking member 100 as shown in FIG. 19 is constructed of stainless steel in the form of a planar base plate 102 with two L shaped cut out recesses 104 with curved ends 105 that allow entry over the plunger or piston rod 67, 77 between the circular segmented portions 68, 78. The locking member locks both plunger assemblies in relation to each other and also allows for varying positions of the same. An extension rod or lock shaft 106 extends transversely outward from the plate 102 through handle slot 40 with the end 107 of the shaft being provided with a plurality of angled cuts to aid in securing the end 107 to knob 108. The lock shaft 106 has an end cap or knob 108 mounted to its distal end over the angled cuts to allow the user to easily move the locking member in a locked and unlocked position which may be indicated on the housing by markings or color indicia as shown in FIG. 2. The position of piston assemblies 60 and 70 in the locking member 100 is shown in phantom in FIGS. 18 and 19.

The mixing housing 88 defines a lower chamber 82 as seen in FIG. 11 which seats and holds the distal end 43 of rachet bar 42 in a fixed position so that the mixing housing 88 is driven backwards toward the handle 30 causing the pistons to be driven forward in the respective syringe barrels 62 and 72 driving the materials contained therein to be forced out of the respective barrels or tubes along the curved mixing passageways or conduits 85 and 87 in the mixing housing to nozzle connector 90. The nozzle connector member 90 which is shown in FIGS. 5 and 5A is secured to the distal end of the mixing housing 88 and defines a central chamber 92 which is axially aligned with nozzle 200. The nozzle connector member 90 has two opposed flanges 94 which define a space 96 between the bottom of the flanges and the top surface 91 of the connector member. A circular boss 93 surrounds the outlet for the central chamber 92 and extends away from the top surface 91 of the connector to form a seat for nozzle 200. The mixing housing is preferably constructed of the same plastic material as the handle housing and the trigger mechanism.

The nozzle 200 which is removably mounted on the nozzle connector member 90 via the locking flange structure 94 formed on the nozzle connector 90. The nozzle is constructed with a base plate 202 which has two curved ends 204 and linear sides 206 allowing the same to be inserted in the nozzle connector 90 with the bore 208 of the tube of the nozzle being seated over the circular boss 93 of the connector member 90. The nozzle is rotated so that the base plate curved ends 204 are frictionally held within space 96. The nozzle tube has exterior fluting 210 to aid in rotating the nozzle to lock the same in the connector 90. Mounted within the bore of the tube 208 is a helix 212 which is curved at an angle around 30° which reduces the forces acting on the marrow cells as they are mixed and discharged from the nozzle. The nozzle diameter is highly polished and provided clearance for the delivered material. It is important to note that when delivering marrow to the wound site, that cells can be damaged by corners, edges and rough surfaces as well as by force. The present invention allows for a short path for the marrow to travel with no edges and sharp turns. The path surface can be polished or coated with Teflon®, silicone or other low friction material which will lower shear stresses on the cells.

In operation, the surgeon perforates the patient's bone (ilea, vertebra, sternum or long bone condyle). The bone marrow is withdrawn, i.e., aspirated from the bone into the syringe tube 62. This syringe 62 is provided empty and is coated with heparin. This syringe has a luer lock tip 63 which mates with the proximal end of a separate bone marrow aspirate device. The empty, heparin coated syringe is used to withdraw the bone marrow from the patient's bone. Three to five cubic centimeters of bone marrow aspirate (BMA) may be collected in the second syringe. When it is filled, it will be placed into a receiving chamber 84 in the mixing housing and be adjacent and parallel to the first syringe 72 which, in this example holds the premixed demineralized bone material (DBM) and hyaluronic acid (HA) scaffoling material. This mixture is a flowable paste or putty and is within the property range previously disclosed.

A piston or plunger assembly is then placed rearward of the two syringe tubes with the piston head inside the tube and the assembly is inserted into the applicator gun. This plunger is sized to a specific pre-set volume and matches the actual BMA volume chosen and collected.

The operator squeezes the trigger of the applicator device and the rachet drive propels the contents of both syringe tubes simultaneously into and through the mixing tip/nozzle. The bone marrow will intermix with the DBM/HA as they simultaneously pass through the mixing tip/nozzle. The combined materials are then placed in the wound site by the surgeon.

The plunger assemblies shown in FIGS. 6 and 7 can be sized to be compatible with the BMA volume collected and the DBM/HA volume in syringe number. This is achieved by the diameter of the plunger on the number 2 syringe (BMA) side. This dual syringe system provides a simple and precise way to collect, mix and deliver in a sterile manner a mixture of DBM and BMA in a range of 1:1 to 1:6, preferably a 1:3 ratio or BMA to DBM to the wound or bone defect site. Thus, the kit can hold these different sized diameter syringe tubes to allow the surgeon to select the ratio desired.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present inventions defined by the following claims.

We claim:

1. A bone marrow mixing instrument comprising: a handle assembly, a mixing housing connected to said handle assembly, a drive mechanism moveably mounted in said handle assembly and secured to said mixing housing, said mixing housing defining chambers to hold syringe tubes of different diameters and material pathways leading from said chambers to a nozzle section of said mixing housing, piston means including a piston rod and a piston head mounted to said piston rod, said piston rod and piston head being slidably mounted in each of said syringe tubes, trigger means pivotally mounted to said handle housing, said trigger means when pulled causing said drive mechanism to sequentially transport said mixing assembly toward said handle assembly, and a locking means mounted in said handle assembly to lock said piston rods in a fixed position.

2. A bone marrow mixing instrument according to claim 1 wherein said piston means comprises a piston rod having segmented parts and a resilient piston head mounted on said piston rod.

3. A bone marrow mixing instrument according to claim 2 wherein said segmented piston rod has a plurality of spaced circular segments.

4. A bone marrow mixing instrument according to claim 1 wherein said drive mechanism is a rachet drive comprising a rachet bar and a pawl.

5. A bone marrow mixing instrument according to claim 1 wherein said piston head is cone shaped.

6. A bone marrow mixing instrument according to claim 1 wherein said locking means comprises a flat base plate with a plurality of L shaped cutouts formed in said base plate to receive and hold said piston rod, an activator shaft integrally formed with said base plate extending outward from said base plate on the opposite side of said base plate from said L shaped cutouts, said activator shaft extending outside of said handle housing.

7. A bone marrow mixing instrument according to claim 1 wherein said mixing housing nozzle section has a nozzle connecting member said nozzle connecting member defining a central chamber which is adapted to be aligned with a nozzle and a nozzle lock structure.

8. A bone marrow mixing instrument according to claim 7 wherein the distal end of said nozzle connecting member central chamber is formed by a circular boss.

9. A bone marrow mixing instrument according to claim 8 wherein a nozzle member having a central throughgoing bore is adapted to be mounted over said circular boss.

10. A bone marrow mixing instrument according to claim 1 wherein a mixing nozzle is mounted at said nozzle section.

11. A bone marrow mixing instrument according to claim 10 wherein said mixing nozzle has a planar locking plate with two curved opposing ends and linear sides and a nozzle with a central throughgoing bore extending from said plate.

12. A bone marrow mixing instrument according to claim 10 wherein said mixing nozzle defines a throughgoing bore with a helix mounted therein.

13. A bone marrow mixing instrument according to claim 12 wherein said helix is curved at about 30°.

14. A bone marrow mixing instrument according to claim 13 wherein said helix mixes bone marrow to a scaffoling material at ratio of about 1 to about 3.

15. A bone marrow mixing instrument according to claim 13 wherein said helix mixes bone marrow to a scaffoling material at ratio ranging from 1:1 to 1:6.

16. A bone marrow mixing instrument comprising: a handle housing and a trigger mechanism rotatably mounted to said handle housing, said trigger mechanism being biased outward by spring means mounted in said handle housing and engaging said trigger mechanism, a rachet drive mounted in said housing, said ratchet drive including a moveable ratchet bar mounted in said handle housing with the a distal end of said ratchet bar being secured to a mixing housing, said mixing housing defining chambers for receiving syringe tubes and channels communicating with said syringe tube chambers leading to a distal end of said mixing housing, a cartridge dispenser mounted in said syringe chamber, said cartridge dispenser comprising a syringe tube handle, a piston head mounted in said syringe tube and a piston rod mounted to said piston head, a drive mechanism mounted in said handle assembly causing said ratchet bar to be sequentially driven by the action of said trigger mechanism rearward through said handle housing causing each said piston head to move in said syringe barrel to dispense material held in said syringe barrel along said mixing housing channels into and through a nozzle mounted to said mixing housing, said nozzle defining a central throughgoing bore with a helix mixing member mounted therein.

17. A bone marrow mixing instrument according to claim 16 wherein said piston rod is constructed with segmented parts.

18. A bone marrow mixing instrument according to claim 16 wherein said piston rod comprises a plurality of spaced circular segments positioned on a central rod.

19. A bone marrow mixing instrument according to claim 16 wherein said helix mixing member is curved at about 30°.

20. A bone marrow mixing instrument according to claim 16 wherein the distal end of said mixing housing is formed with a nozzle connecting member, said nozzle connecting member defining a central chamber with one end of the chamber being formed by a circular boss on an exterior distal end.

21. A bone marrow mixing instrument according to claim 20 wherein a nozzle member having a central throughgoing bore is adapted to be mounted over said circular boss.

22. A bone marrow mixing instrument according to claim 16 wherein said mixing housing chamber is cylindrical and have different chambers, helix mixing member mixes bone marrow and a scaffolding material and discharge same at a ratio of about 1 to about 3.

23. A bone marrow mixing instrument according to claim 16 wherein bone marrow and a scaffolding material are contained in said syringe tubes and the same are applied to a bone defect material at a ratio of about 1 to about 3.

24. A bone marrow mixing instrument comprising: a handle housing and a trigger member moveably mounted to said handle housing, said trigger member being biased outward from said handle housing by spring means mounted in said handle housing and engaging said trigger member, a rachet drive mounted in said handle housing, said rachet drive including a toothed rachet member moveably mounted in said handle housing with a pawl member mounted on said trigger member engaging said ratchet bar causing said ratchet bar to be sequentially driven when said trigger member is pulled toward said handle housing rearward through said handle housing, a distal end of said ratchet bar being secured to a mixing housing, said mixing housing defining a ratchet bar receiving chamber, a plurality of chambers for receiving syringe barrels of different diameters and conduit pathways communicating with said syringe barrel chambers and leading a discharge conduit located at a distal end of said mixing housing, a cartridge material dispenser mounted in each of said syringe chambers, said cartridge material dispenser comprising a syringe barrel, a piston head mounted in said syringe barrel and a piston rod mounted to said piston head, said ratchet bar when sequentially driven by the action of said trigger member and associated pawl member rearward toward said handle housing transporting said mixing housing causing each piston head mounted in said syringe barrel to move in said syringe barrel toward a tip of said syringe barrel to dispense material held in each of said syringe barrels through said mixing housing channels into and through a nozzle mounted to said mixing housing.

25. A bone marrow mixing instrument according to claim 24 wherein said handle housing comprises a drive section and an integral hand grip section extending from said drive section.

26. A bone marrow mixing instrument according to claim 24 wherein said piston rod is segmented with a plurality of spaced circular segments which extend outward from a central rod member.

27. A bone marrow mixing instrument according to claim 24 wherein said nozzle has a helix mixing member mounted therein.

28. A bone marrow mixing instrument according to claim 24 wherein said trigger member is of a shorter length than a hand grip of said handle housing and fits within a protrusion extending outward from said handle grip.

29. A bone marrow mixing instrument according to claim 24 wherein a locking member is moveably mounted to said handle housing for engagement with said piston rods, said locking member comprising a flat base plate with a plurality of L shaped cutouts formed in said base plate to receive and hold said piston rod, an activator shaft integrally formed with said base plate extending outward from said base plate on the opposite side of said base plate from said L shaped cutouts, said activator shaft extending outside of said handle housing.

30. A bone marrow mixing instrument according to claim 29 wherein said activator shaft knob has a member mounted on a distal end.

31. A bone marrow mixing instrument according to claim 24 wherein said nozzle comprises a planar base plate with a length which is longer than its width, a tube with a throughgoing bore mounted to said base plate, said tube having a curved helix mounted therein.

32. A bone marrow mixing instrument according to claim 31 wherein said tube has a plurality of flutes running along its length.

33. A bone marrow mixing instrument according to claim 24 wherein said handle housing has a connector member positioned on its distal end to hold said nozzle.

34. A bone marrow mixing instrument according to claim 33 wherein connector member defines a circular boss located around an exit aperture and a plurality of opposing bent back flanges which form a space between the bottom of the flange and the top surface of the connector member to hold said nozzle.

35. A bone marrow mixing instrument according to claim 24 wherein said handle housing defines a post located above said pawl member a coil spring mounted around said post which engages said pawl member to bias said pawl member downward.

36. A bone marrow mixing instrument according to claim 24 wherein each piston head defines an internal stepped chamber with a blind central bore.

37. A bone marrow mixing instrument according to claim 24 wherein said each piston head has a body shaped as a cone with a tip extending from said cone shaped body.

38. A bone defect material mixing instrument comprising: a handle housing, a trigger member pivotally mounted to said handle housing, said trigger member being biased outward from said handle housing by spring means mounted in said handle housing and engaging said trigger member, a ratchet bar moveably mounted in said handle housing, a ratchet drive having a pawl member mounted on said trigger member engaging said ratchet bar causing said ratchet bar to be sequentially driven by the action of said trigger member rearward through said handle housing when said trigger member is pulled against said handle housing, a distal end of said ratchet bar being secured to a mixing housing, said mixing housing defining a ratchet bar receiving chamber, a plurality of chambers for receiving syringe tubes of different diameters and conduit pathways communicating with said syringe tube chambers and leading to a distal end of said mixing housing, a cartridge material dispenser mounted in said syringe chamber, said cartridge material dispenser comprising a syringe barrel, sterile flowable material for application to a bone defect area contained within said barrel, a piston head mounted in said syringe barrel and a piston rod mounted to said piston head, said pawl member engaging said ratchet bar and causing said ratchet bar to be sequentially driven by the action of said trigger member rearward toward said handle housing carrying said mixing housing and causing each said piston head mounted in said syringe barrel to move in said syringe barrel toward a tip of said syringe barrel to dispense material held in said syringe barrel along said channels into and through a nozzle mounted to said mixing housing, said nozzle defining a central throughgoing bore with a helix mixing member mounted therein.

\* \* \* \* \*

UNITED STATES PATENT AND TRADEMARK OFFICE
CERTIFICATE OF CORRECTION

PATENT NO.         : 7,018,382 B1                                       Page 1 of 1
APPLICATION NO. : 10/740813
DATED              : March 28, 2006
INVENTOR(S)        : Barbara L. Merboth and Arthur A. Gertzman It is certified that error appears in the above-identified patent and that said Letters Patent is hereby corrected as shown below:

Title page,
Item [75], Inventors, "Genzman" should read -- Gertzman --.

Signed and Sealed this

Twenty-seventh Day of June, 2006

JON W. DUDAS
*Director of the United States Patent and Trademark Office*